(12) United States Patent
Itai

(10) Patent No.: US 9,713,504 B2
(45) Date of Patent: Jul. 25, 2017

(54) SURGERY ASSISTANCE APPARATUS AND METHOD, AND NON-TRANSITORY RECORDING MEDIUM HAVING STORED THEREIN SURGERY ASSISTANCE PROGRAM

(71) Applicant: FUJIFILM CORPORATION, Tokyo (JP)

(72) Inventor: Yoshinori Itai, Tokyo (JP)

(73) Assignee: FUJIFILM Corporation, Minato-Ku, Tokyo (JP)

( * ) Notice: Subject to any disclaimer, the term of this patent is extended or adjusted under 35 U.S.C. 154(b) by 22 days.

(21) Appl. No.: 14/859,565

(22) Filed: Sep. 21, 2015

(65) Prior Publication Data

US 2016/0008085 A1    Jan. 14, 2016

Related U.S. Application Data

(63) Continuation of application No. PCT/JP2014/000359, filed on Jan. 24, 2014.

(30) Foreign Application Priority Data

Mar. 27, 2013  (JP) ................................. 2013-065441

(51) Int. Cl.
    *G06K 9/00* (2006.01)
    *A61B 19/00* (2006.01)
    (Continued)

(52) U.S. Cl.
    CPC .............. *A61B 19/50* (2013.01); *A61B 5/489* (2013.01); *A61B 6/504* (2013.01); *A61B 6/5211* (2013.01);
    (Continued)

(58) Field of Classification Search
    None
    See application file for complete search history.

(56) References Cited

U.S. PATENT DOCUMENTS

| 2012/0053443 | A1* | 3/2012 | Sakuragi | A61B 19/50 600/407 |
|---|---|---|---|---|
| 2012/0209103 | A1 | 8/2012 | Sakuragi | |
| 2013/0144160 | A1 | 6/2013 | Sakuragi | |

FOREIGN PATENT DOCUMENTS

| JP | 2001-283191 A | 10/2001 |
|---|---|---|
| JP | 2003-339644 A | 12/2003 |

(Continued)

OTHER PUBLICATIONS

Communication dated Feb. 23, 2016 from the Japanese Patent Office in counterpart application No. 2013-065441.
(Continued)

*Primary Examiner* — Hadi Akhavannik
(74) *Attorney, Agent, or Firm* — Sughrue Mion, PLLC

(57) ABSTRACT

A surgery assistance apparatus includes an organ region extraction unit that extracts a tubular-organ region from a three-dimensional image obtained by imaging a tubular-organ and a blood vessel dominating the tubular-organ, a blood vessel region extraction unit that extracts a blood vessel region dominating the tubular-organ from the three-dimensional image, a branching structure extraction unit that extracts a branching structure of the blood vessel from the extracted blood vessel region, and a dominated region identification unit that identifies, with respect to an arbitrary partial blood vessel corresponding to an upper edge branching at least once to reach an edge including a terminal-end of the extracted branching structure, a dominated region in the tubular-organ region that is dominated by the arbitrary partial blood vessel by using positional relationships between a plurality of terminal end points present after the (Continued)

edge of the arbitrary partial blood vessel branches last and the tubular-organ region.

13 Claims, 4 Drawing Sheets

(51) Int. Cl.
| | |
|---|---|
| *A61B 5/00* | (2006.01) |
| *A61B 6/00* | (2006.01) |
| *G06K 9/46* | (2006.01) |
| *G06T 7/00* | (2017.01) |
| *A61B 34/10* | (2016.01) |
| *G06T 7/73* | (2017.01) |
| *A61B 5/055* | (2006.01) |
| *A61B 6/03* | (2006.01) |

(52) U.S. Cl.
CPC ............ *A61B 34/10* (2016.02); *G06K 9/4604* (2013.01); *G06T 7/0012* (2013.01); *G06T 7/73* (2017.01); *A61B 5/004* (2013.01); *A61B 5/055* (2013.01); *A61B 6/032* (2013.01); *A61B 2034/101* (2016.02); *A61B 2034/107* (2016.02); *A61B 2576/02* (2013.01); *G06T 2200/04* (2013.01); *G06T 2207/10012* (2013.01); *G06T 2207/10072* (2013.01); *G06T 2207/10081* (2013.01); *G06T 2207/10088* (2013.01); *G06T 2207/30028* (2013.01); *G06T 2207/30056* (2013.01); *G06T 2207/30101* (2013.01)

(56) References Cited

FOREIGN PATENT DOCUMENTS

| | | |
|---|---|---|
| JP | 2009-165718 A | 7/2009 |
| JP | 2012-165910 A | 9/2012 |
| WO | 2012/020547 A1 | 2/2012 |

OTHER PUBLICATIONS

Toyofumi Saito, et al., "An Improvement of Three-Dimensional Thinning Method Using a Skeleton Based on the Euclidean Distance Transformation—A Method to Control Spurious Branches-", Journal of the Institute of Electronics, Information and Communication Engineers, D-II, 2001, pp. 1628-1635, vol. J84-D-II, No. 8.
Masahiro Yasue, et al., "Thinning Algorithms for Three Dimensional Gray Images and Their Application to Medical Images with Comparative Evaluation of Performance", Journal of the Institute of Electronics, Information and Communication Engineers, D-II, 1996, pp. 1664-1674, vol. J79-D-II, No. 10.
International Search Report of PCT/JP2014/000359, dated May 27, 2014. [PCT/ISA/210].
Written Opinion of PCT/JP2014/000359, dated May 27, 2014. [PCT/ISA/237].

\* cited by examiner

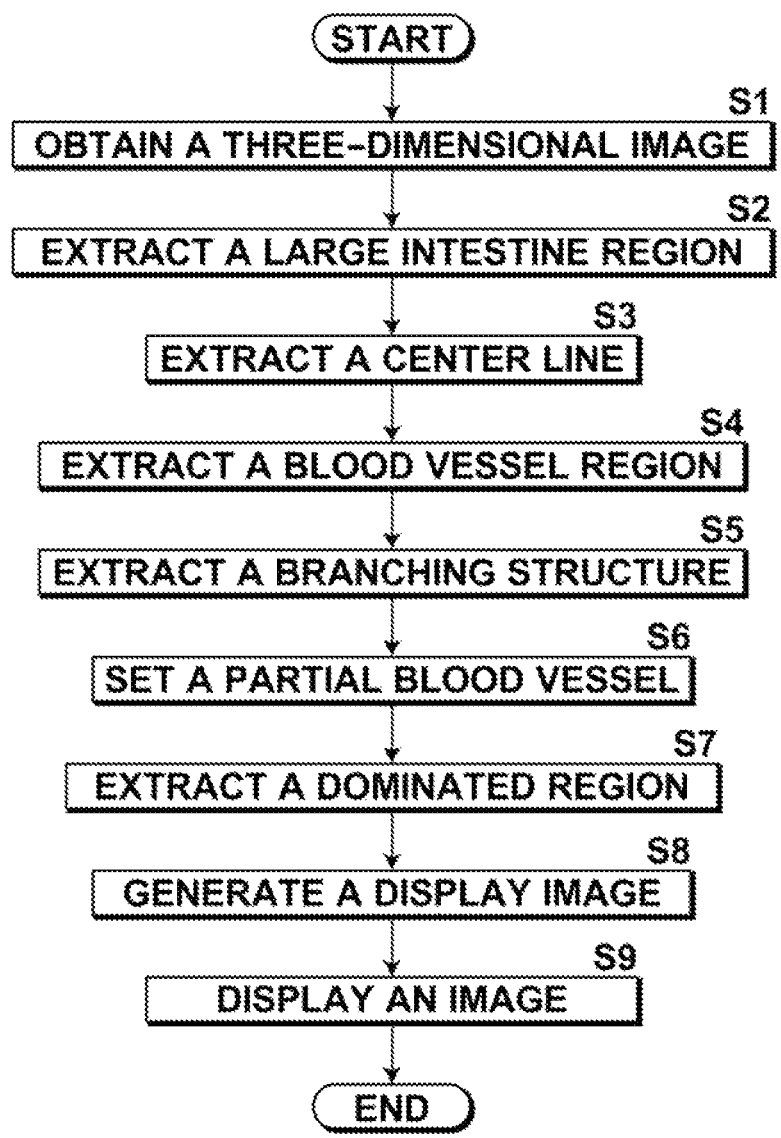

SURGERY ASSISTANCE APPARATUS AND METHOD, AND NON-TRANSITORY RECORDING MEDIUM HAVING STORED THEREIN SURGERY ASSISTANCE PROGRAM

CROSS-REFERENCE TO RELATED APPLICATIONS

This application is a Continuation of PCT International Application No. PCT/JP2014/000359 filed on Jan. 24, 2014, which claims priority under 35 U.S.C. §119(a) to Japanese Patent Application No. 2013-065441 filed on Mar. 27, 2013. Each of the above applications is hereby expressly incorporated by reference, in its entirety, into the present application.

BACKGROUND

The present disclosure relates to a surgery assistance apparatus, method and program for assisting a doctor in determining a region to be excised when an excision is performed on a tubular organ, such as a large intestine and bronchi.

In medical fields, when a diseased part, such as a tumor, is excised in a surgery, the part to be excised is appropriately determined before the surgery by diagnosis based on images. For example, Japanese Unexamined Patent Publication No. 2001-283191 (Patent Document 1) and Japanese Unexamined Patent Publication No. 2003-339644 (Patent Document 2) propose techniques for assisting by a computer. In Patent Document 1 and Patent Document 2, a blood vessel branch that supplies nutrition to a diseased part is identified in a three-dimensional X-ray CT (Computed Tomography) image of a liver by identifying, based on three-dimensional distances between voxels constituting the liver parenchyma and voxels constituting blood vessels running in the liver, a voxel of the blood vessels dominating each of voxels of the liver parenchyma. Further, a set of voxels of the liver parenchyma dominated by the blood vessel branch is determined as a part to be excised.

SUMMARY

However, in the techniques proposed in Patent Document 1 and Patent Document 2, an excision region is determined by using a structural characteristic of the liver that a blood vessel dominating the organ, in other words, a blood vessel supplying oxygen and nutrition to the organ (hereinafter, referred to as "nutrition blood vessel") runs into the organ. Therefore, the techniques are not applicable to an organ, such as a large intestine and bronchi, the nutrition blood vessel of which runs outside the organ. However, realization of an assistance technique by a computer is expected in determining a region to be excised also for the organ, such as the large intestine and bronchi.

In view of the foregoing circumstances, the present disclosure provides a surgery assistance apparatus, method and program that can assist a doctor in determining a region to be excised when an excision is performed on a tubular organ, such as a large intestine and bronchi.

To solve the aforementioned problem, a surgery assistance apparatus of the present disclosure includes an organ region extraction means that extracts a tubular organ region from a three-dimensional image obtained by imaging a tubular organ and a blood vessel dominating the tubular organ, a blood vessel region extraction means that extracts a blood vessel region dominating the tubular organ from the three-dimensional image, a branching structure extraction means that extracts a branching structure of the blood vessel from the extracted blood vessel region, and a dominated region identification means that identifies, with respect to an arbitrary partial blood vessel corresponding to an upper edge branching at least once to reach an edge including a terminal end of the extracted branching structure, a dominated region in the tubular organ region that is dominated by the arbitrary partial blood vessel by using positional relationships between plural terminal end points present after the edge of the arbitrary partial blood vessel branches last and the tubular organ region.

Here, the "tubular structure" means an organ having a tubular or sac-shaped form, and a stomach, a large intestine, a rectum, bronchi, a urinary bladder and the like are included. However, blood vessels are not included. Further, the expression "dominating the organ" means keeping the function of the organ normal by supplying oxygen and nutrition to the organ. Further, the expression "store a three-dimensional image" means storing image data representing the three-dimensional image.

Further, the "terminal end point" means a terminal end or a point present within a range that may be substantially regarded as the terminal end. For example, a point within the range of 30 mm from a terminal end may be regarded as a terminal end point. Further, the "positional relationships of the terminal end points with the tubular organ region" include positional relationships between the terminal end points and the tubular organ region itself, positional relationships between the terminal end points and a surface of the tubular organ region (a curved surface region), positional relationships between the terminal end points and a center line (a linear region) of the tubular organ region, and the like.

The surgery assistance apparatus of the present disclosure may include a center line extraction means that extracts a center line of the tubular organ region. Further, the dominated region identification means may determine a corresponding point on the center line corresponding to each of the plural terminal end points by using positional relationships between the plural terminal end points and the center line, and obtain cross sections that pass through two outermost corresponding points of the determined plural corresponding points, respectively, or points in the vicinities of the outermost corresponding points, respectively, and that are orthogonal to the center line, and identify a part of the tubular organ region between the cross sections, as the dominated region.

Here, the "points in the vicinities of the corresponding points" mean a point within the range of 30 mm in the direction of the center line from a corresponding point.

The surgery assistance apparatus of the present disclosure may include an image generation means that generates, from the three-dimensional image, an image representing the identified dominated region and a rest of the tubular organ region in a manner visually distinguishable from each other.

In the surgery assistance apparatus of the present disclosure, the dominated region identification means may receive specification of an arbitrary position by a user on an upper edge branching at least once to reach an edge at a terminal end of the branching structure, and identify, with respect to a partial blood vessel corresponding to the edge at the specified position, the dominated region dominated by the partial blood vessel.

In the surgery assistance apparatus of the present disclosure, the dominated region identification means may determine a point on the center line at a shortest distance from each of the terminal end points, as a corresponding point corresponding to each of the terminal end points. Alternatively, the dominated region identification means may obtain a point on a surface of the tubular organ region at a shortest distance from each of the terminal end points, and determine a point on the center line at a shortest distance from the obtained point, as a corresponding point corresponding to each of the terminal end points.

Further, the dominated region identification means may determine positions of the cross sections orthogonal to the center line in the direction of the center line in such a manner that the dominated region becomes larger as the partial blood vessel has a greater representative value of diameter.

Here, the "representative value of diameter of the partial blood vessel" may be the largest value or the smallest value of the diameter of the highest edge in the partial blood vessel or an average of diameters at plural positions on the edge. When a position has been specified by a user, the representative value may be the diameter at the specified position. Alternatively, the representative value may be an average of diameters of at least two lowest edges in the partial blood vessel.

In the surgery assistance apparatus of the present disclosure, the dominated region identification means may receive specification of an arbitrary position by a user on an upper edge branching at least once to reach an edge at a terminal end of the branching structure, and identify, with respect to a partial blood vessel corresponding to the edge at the specified position, the dominated region dominated by the partial blood vessel. Further, the apparatus may include an image generation means that generates, from the three-dimensional image, an image representing a partial blood vessel region corresponding to a segment from the specified position to all of terminal ends present after the specified position branches last and a rest of the blood vessel region in a manner visually distinguishable from each other and also representing the identified dominated region and a rest of the tubular organ region in a manner visually distinguishable from each other.

A surgery assistance method of the present disclosure causes one or plural computers to execute a procedure performed by each means of the surgery assistance apparatus of the present disclosure.

A surgery assistance program of the present disclosure causes one or plural computers to function as each means of the surgery assistance apparatus of the present disclosure. This program may be stored in a recording medium, such as a CD-ROM and a DVD, or stored in a storage attached to a server computer or a network storage in a downloadable manner, and provided for a user.

A surgery assistance apparatus, method and program of the present disclosure extracts a tubular organ region from a three-dimensional image obtained by imaging a tubular organ and a blood vessel dominating the tubular organ, and extracts a blood vessel region dominating the tubular organ from the three-dimensional image, and extracts a branching structure of the blood vessel from the extracted blood vessel region, and identifies, with respect to an arbitrary partial blood vessel corresponding to an upper edge branching at least once to reach an edge including a terminal end of the extracted branching structure, a dominated region in the tubular organ region that is dominated by the arbitrary partial blood vessel by using positional relationships between plural terminal end points present after the edge of the arbitrary partial blood vessel branches last and the tubular organ region. This identified region represents a range that is sufficiently large as a target region of excision when excision is performed by clipping the partial blood vessel, or the like. Therefore, a doctor can appropriately and easily determine, based on this identified dominated region, a part to be removed in excision.

BRIEF DESCRIPTION OF THE DRAWINGS

FIG. 8 is a flow chart showing processing performed at the image diagnosis assistance system.

DESCRIPTION OF THE PREFERRED EMBODIMENTS

Figure 1:
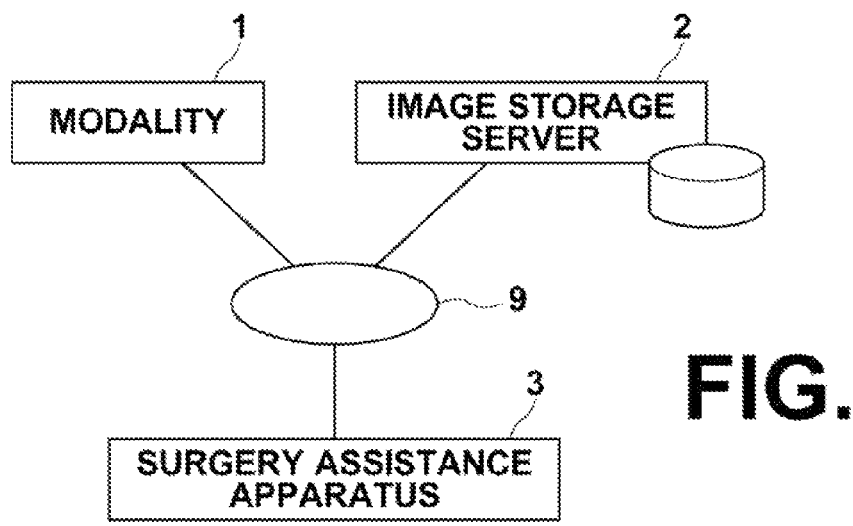
FIG. 1 is a schematic diagram illustrating the configuration of an image diagnosis assistance system to which a surgery assistance apparatus of the present disclosure has been introduced.

Hereinafter, an image diagnosis assistance system to which a surgery assistance apparatus according to an embodiment of the present disclosure has been introduced will be described. FIG. 1 is a schematic diagram illustrating the hardware configuration of this image diagnosis assistance system. As illustrated in FIG. 1, in this system, a modality 1, an image storage server 2 and a surgery assistance apparatus 3 are connected to each other through a network 9 in such a manner that they can communicate with each other.

The modality 1 is an apparatus that generates image data of a three-dimensional image representing a region to be examined of a subject by imaging the region, and outputs, as image information, the image data by attaching supplementary information defined in a standard, such as DICOM (Digital Imaging and Communications in Medicine), to the image data. Specific examples of the modality 1 are a CT (Computed Tomography) apparatus, an MRI (Magnetic Resonance Imaging) apparatus and the like.

The image storage server 2 is a computer that stores image data obtained at the modality 1 and image data generated by image processing at the surgery assistance apparatus 3 in an image database, and manages the image data. The image storage server 2 includes a large capacity external storage device and software for managing the database (for example, ORDB (Object Relational Database) management software).

The surgery assistance apparatus 3 is a computer including a central processing unit (CPU) and a storage, such as a semiconductor memory and a hard disk, an SSD (Solid State Drive) or the like in which a surgery assistance program according to an embodiment of the present disclosure has been installed. The surgery assistance program defines an organ region extraction procedure, a center line extraction procedure, a blood vessel region extraction procedure, a branching structure extraction procedure, a dominated region identification procedure and image generation procedure, as procedures to be executed by a CPU of a computer. Further, the surgery assistance apparatus 3 is connected to an input device, such as a mouse and a keyboard, and a display device, such as a display.

Figure 2:
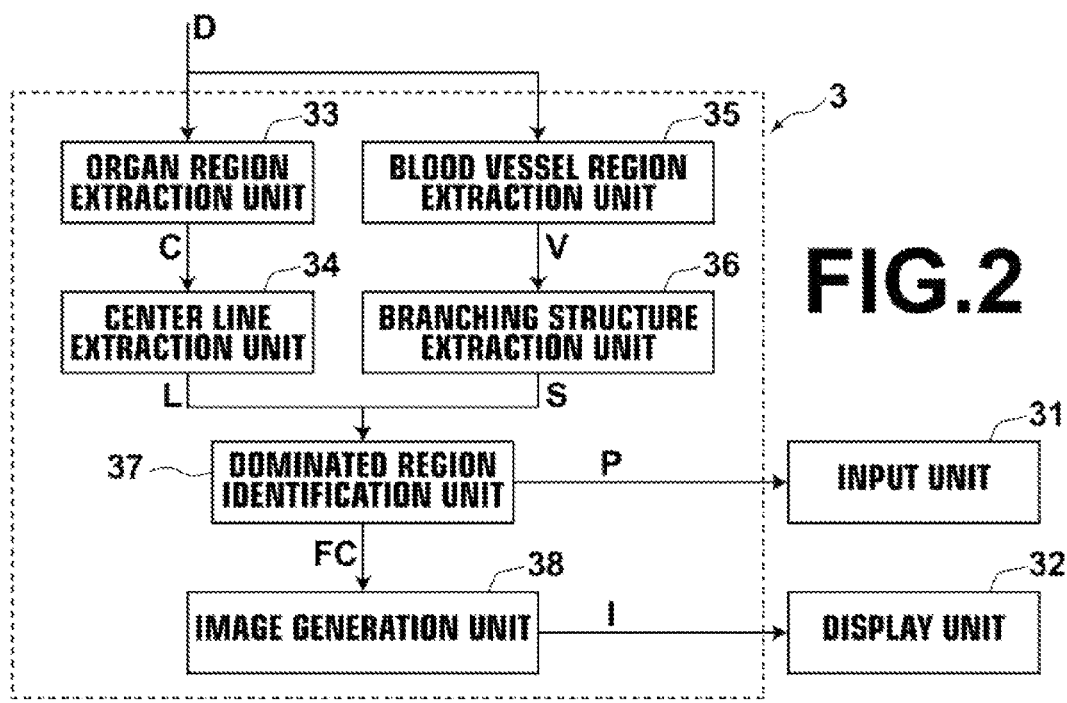
FIG. 2 is a functional block diagram of a surgery assistance apparatus according to an embodiment of the present disclosure.

FIG. 2 is a block diagram dividing the surgery assistance apparatus 3 at a function level. As illustrated in FIG. 2, the surgery assistance apparatus 3 includes an organ region extraction unit 33, a center line extraction unit 34, a blood vessel region extraction unit 35, a branching structure extraction unit 36, a dominated region identification unit 37, an image generation unit 38, an input unit 31 and an output unit 32. The function of each processing unit in the frame indicated by a broken line is achieved by execution of the surgery assistance program by the CPU. The input unit 31 is achieved by an input device, and the output unit 32 is achieved by an output device.

The organ region extraction unit 33 receives three-dimensional image D, which was obtained by imaging target tubular organ and a blood vessel dominating tubular organ, and extracts a tubular organ region of a subject to be examined from three-dimensional image D. The tubular organ is, for example, a stomach, a large intestine, a rectum, bronchi, a urinary bladder, and the like. In the embodiment of the present disclosure, large intestine region C is extracted. As a method for extracting the large intestine region from the three-dimensional image, specifically, first, plural axial slice images are generated at cross sections (axial slice; axial) perpendicular to the body axis based on the three-dimensional image. Further, processing for separating an outside region of a body and an inside region of the body from each other with respect to the surface of the body is performed for each of the axial slice images by using a known method. For example, binarization processing is performed on the received axial slice images, and outlines are extracted by outline extraction processing, and an inside of the extracting outlines is extracted as the inside region (of a human body). Then, binarization processing based on a threshold is performed on the axial slice images of the inside region of the body, and a candidate for the large intestine region in each of the axial slice images is extracted. Specifically, binarization processing is performed by setting a threshold (for example, −600 or less) corresponding to the CT value of air, because air is present in the tube of the large intestine, and the air region in the inside region of the body is extracted, as the candidate for the large intestine region, from each of the axial slice images. Finally, the large intestine region is extracted by extracting only a part in which the extracted candidates for the large intestine in the body continue between pieces of the axial slice image data. Here, the method for extracting the large intestine region is not limited to the above method. Various other image processing methods, such as a Region Growing method and a Level Set method, may be used.

The center line extraction unit 34 receives a tubular organ region extracted by the organ region extraction unit 33, and extracts a center line of the tubular organ region. In the embodiment of the present disclosure, the center line of the large intestine is obtained by performing thinning on large intestine region C extracted as described above. Regarding thinning processing, known methods may be adopted. For example, methods disclosed in M. Yasue et al., "Thinning Algorithms for Three-Dimensional Gray Images and Their Application to Medical Images with Comparative Evaluation of Performance", Journal of the Institute of Electronics, Information and Communication Engineers, D-II, Vol. J79-D-II, No. 10, pp. 1664-1674, 1996 and T. Saito et al., "An Improvement of Three Dimensional Thinning Method Using a Skeleton Based on the Euclidean Distance Transformation—A Method to Control Spurious Branches—", Journal of the Institute of Electronics, Information and Communication Engineers, D-II, Vol. J84-D-II, No. 8, pp. 1628-1635, 2001, and the like may be used.

The blood vessel region extraction unit 35 receives three-dimensional image D, and extracts blood vessel region V that dominates a target tubular organ from three-dimensional image D. For example, the blood vessel region extraction unit 35 may extract the blood vessel region from the target three-dimensional image by using a Region Growing method based on an arbitrary seed point set by the user in the blood vessel region. Here, the method for extracting the blood vessel region V is not limited to the aforementioned method. Other various image processing methods, such as a threshold method and a Level Set method, may be used.

Figure 3:
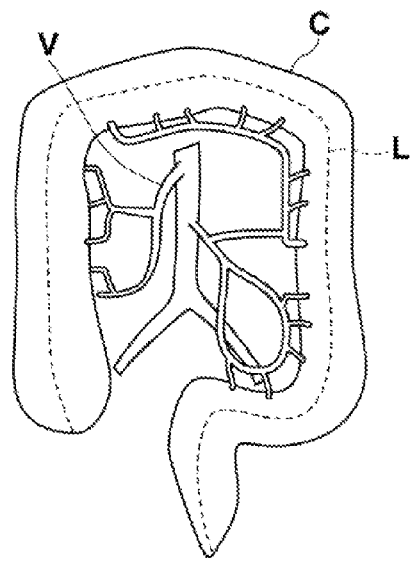
FIG. 3 is a schematic diagram illustrating a large intestine region and its center line and a blood vessel region.

Each extraction processing is performed by the organ region extraction unit 33, the center line extraction unit 34 and the blood vessel region extraction unit 35, as described above. Consequently, it becomes a state in which each of large intestine region C, center line L of large intestine region C and blood vessel region V has been extracted, as schematically illustrated in FIG. 3.

Figure 5:
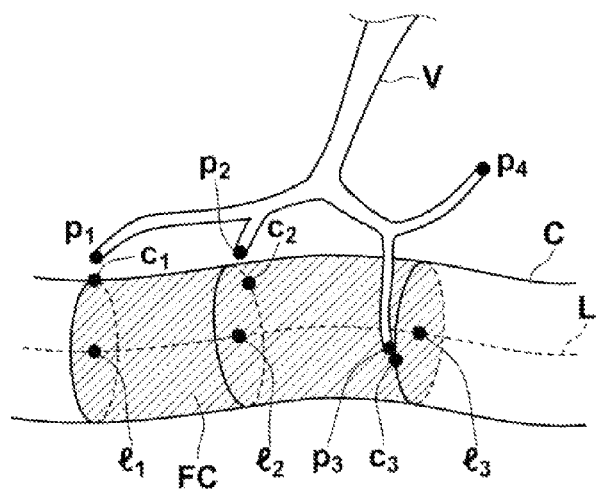
FIG. 5 is a diagram for explaining processing for determining a corresponding point on a center line corresponding to each terminal end point.

The branching structure extraction unit 36 receives blood vessel region V extracted by the blood vessel region extraction unit 35, and extracts branching structure S of the blood vessel from blood vessel region V. For example, the branching structure extraction unit 36 performs thinning processing on the extracted blood vessel region V. The branching structure extraction unit 36 extracts branching structure S (for example, a tree structure) of the blood vessel, as illustrated in FIG. 5, by classifying, based on the connection relationship of the obtained thin lines, voxels on the thin lines into an end point, an edge and a branching point. Further, feature values, such as the diameter of a blood vessel at each voxel on the thin lines and the length of each edge (blood vessel branch), may also be stored as branching structure data, if necessary.

The dominated region identification unit 37 identifies, with respect to an arbitrary partial blood vessel corresponding to an upper edge branching at least once to reach an edge including a terminal end of branching structure S extracted by the branching structure extraction unit 36, a dominated region in large intestine region C that is dominated by the arbitrary partial blood vessel by using positional relationships between plural terminal end points present after the edge of the arbitrary partial blood vessel branches last and large intestine region C.

Figure 4:
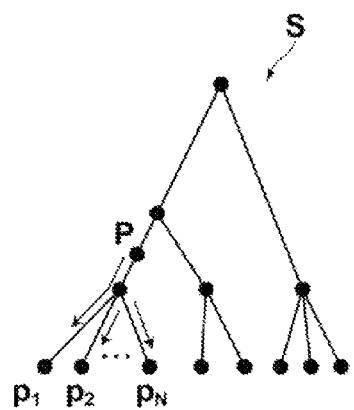
FIG. 4 is a diagram for explaining processing for obtaining terminal end points by using a branching structure of a blood vessel.

For example, first, specification by a user of arbitrary position P on an upper edge branching at least once to reach an edge at a terminal end of a branching structure is received at the input unit 31. Then, plural terminal end points $p_1$, $p_2$, ... $p_N$ (N is a natural number greater than or equal to 2), which are present after the edge at position P branches last, are identified by following branching structure S, as illustrated in FIG. 4, from specified position P toward the downstream side. Then, corresponding points $l_1$, $l_2$, ... $l_M$ (M is a natural number less than or equal to N) on center line L corresponding to terminal end points $p_1$, $p_2$, ... $p_N$, respectively, are determined by using positional relationships between plural terminal end points $p_1$, $p_2$, ... $p_N$ and center line L.

At this time, when a terminal end point or points located away from the surface of large intestine region C by a predetermined distance or more (for example, 50 mm or more) are present in plural terminal end points $p_1, p_2, \ldots p_N$, it is desirable that such terminal point or points are excluded from the target for determining a corresponding point. Further, when a terminal end point or points having a length to the first upstream branching point therefrom longer than or equal to a predetermined length (for example, 100 mm or more) are present in plural terminal end points $p_1, p_2, \ldots p_N$, it is desirable that such terminal point or points are also excluded from the target for determining a corresponding point.

Here, a corresponding point corresponding to a terminal end point is determined by obtaining a point on the surface of large intestine region C at a shortest distance from the target terminal end, and by determining, as the corresponding point, a point on the center line at a shortest distance from each obtained point. For example, as illustrated in FIG. 5, points $c_1$ through $c_3$ on the surface of large intestine region C at shortest distances from terminal end points $p_1$ through $p_3$, respectively, are obtained. Terminal end points $p_1$ through $p_3$ of terminal end points $p_1$ through $p_4$ are located within a predetermined range of distance from the surface of large intestine region C. Further, points $l_1$ through $l_3$ on the center line at shortest distances from points $c_1$ through $c_3$, respectively, are determined as corresponding points corresponding to terminal end points $p_1$ through $p_3$.

Then, cross sections that pass through two outermost corresponding points of the determined plural corresponding points $l_1, l_2, \ldots l_M$, respectively, and that are orthogonal to center line L are obtained. Here, the term "outermost" refers to outermost corresponding points on center line L. Further, a part of large intestine region C between the cross sections is identified as dominated region FC. In the example illustrated in FIG. 5, a region of the large intestine between cross sections that pass through two outermost corresponding points $l_1$ and $l_3$, respectively, and that are orthogonal to center line L is identified, as dominated region FC.

The image generation unit 38 generates, from three-dimensional image D, display image I representing a region including at least dominated region FC identified by the dominated region identification unit 37, a blood vessel region dominating dominated region FC and a region around them in such a manner that dominated region FC and the rest of large intestine region C are visually distinguishable from each other. Specifically, mask data representing dominated region FC and the rest of large intestine region C, respectively, and templates defining colors and opacities of dominated region FC and the rest of large intestine region C are prepared in advance. Known volume rendering is performed on three-dimensional image D by using these mask data and templates, and thereby ray casting is performed on regions masked by the pieces of mask data, respectively, by using colors and opacities assigned to structures to be masked, respectively. Accordingly, display image I is generated. At this time, display image I may represent a blood vessel region dominating dominated region FC and the rest of blood vessel region V in a manner distinguishable from each other.

Figure 6:
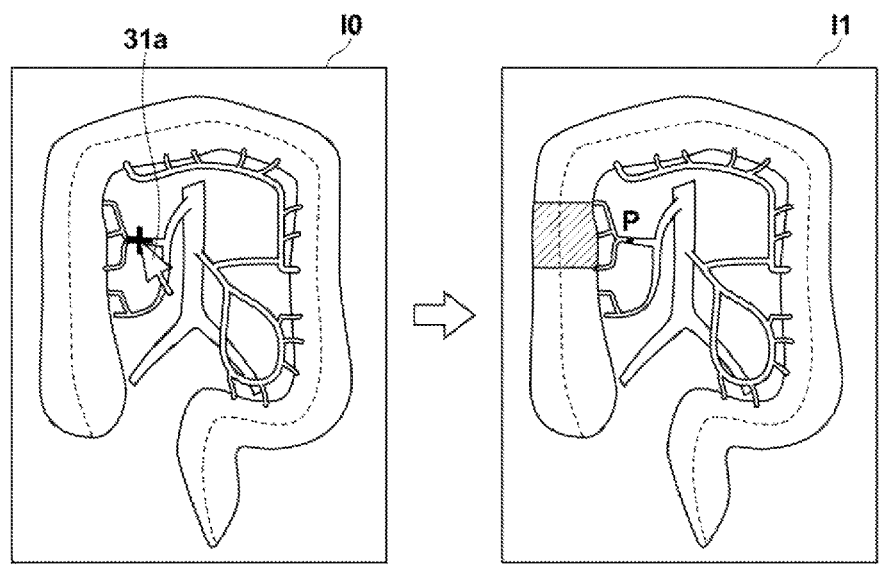
FIG. 6 is a diagram illustrating an example of generation of a display image at an image generation unit.
Figure 7:
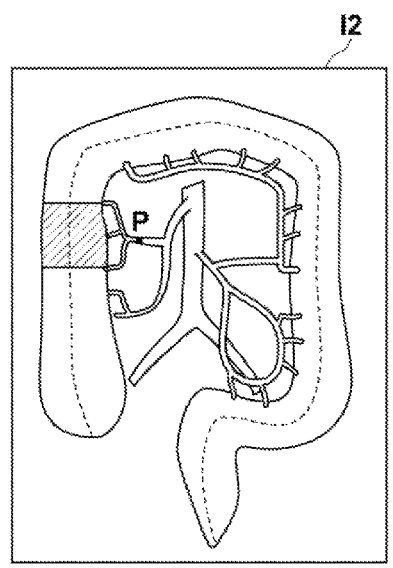
FIG. 7 is a diagram illustrating another example of generation of a display image at an image generation unit.

Further, when specification of position P by a user has been received in dominated region identification processing by the dominated region identification unit 37, the image generation unit 38 may generate display image I representing a partial blood vessel region corresponding to a segment from position P to all of terminal ends present after position P branches last and the rest of blood vessel region V in a manner visually distinguishable from each other and also representing dominated region FC and the rest of large intestine region C in a manner visually distinguishable from each other. Needless to say, only for large intestine region C, dominated region FC and the rest of a region may be displayed in a manner visually distinguishable from each other. For example, when display image JO, as illustrated in the left section of FIG. 6, is displayed on a display screen, if a user specifies position P in a blood vessel region by operating a cursor 31a by a mouse, display image I1, as illustrated in the right section of FIG. 6, may be generated and displayed. In display image I1, visually distinguishable display is performed only for the large intestine region. Alternatively, display image I2, as illustrated in FIG. 7, may be generated and displayed. In display image I2, visually distinguishable display is performed for both of the large intestine region and the blood vessel region.

Next, with reference to a flow chart illustrated in FIG. 8, a flow of processing in the image diagnosis assistance system according to an embodiment of the present disclosure will be described. First, three-dimensional image D (image data) is obtained (S1). Here, three-dimensional image D has been obtained by imaging at the modality 1 based on an examination order from a doctor in a clinical department, who requested imaging, and stored in the image storage server 2. A user operates an operation terminal interface of a known ordering system installed in the surgery assistance apparatus 3, and requests obtainment of three-dimensional image D to be processed. The surgery assistance apparatus 3 sends, based on this operation, a request for retrieval of three-dimensional image D to the image storage server 2. The image storage server 2 obtains three-dimensional image D to be processed by retrieving three-dimensional image D from a database, and sends obtained three-dimensional image D to the surgery assistance apparatus 3. Then, the surgery assistance apparatus 3 obtains three-dimensional image D sent from the image storage server 2.

In the surgery assistance apparatus 3, the organ region extraction unit 33 receives three-dimensional image D, and extracts large intestine region C of a subject to be examined from three-dimensional image D (S2). The center line extraction unit 34 extracts the center line of the large intestine by performing thinning on extracted large intestine region C (S3). Meanwhile, the blood vessel region extraction unit 35 receives three-dimensional image D, and extracts blood vessel region V dominating the large intestine from three-dimensional image D (S4). Further, the branching structure extraction unit 36 extracts branching structure S of the blood vessel from extracted blood vessel region V (S5). Here, it is not always necessary that processing in these steps S2 and S3 and processing in these steps S4 and S5 are performed in the mentioned order. These kinds of processing may be performed simultaneously. Alternatively, processing in steps S4 and S5 may be performed first, and processing in steps S2 and S3 may be performed after then.

When a partial blood vessel, as a target of dominated region identification processing, is set based on specification of arbitrary position P on an upper edge branching at least once to reach an edge at a terminal end of the branching structure by a user, or the like (S6), the dominated region identification unit 37 determines corresponding points $l_1, l_2, \ldots l_M$ on center line L corresponding to plural terminal end points $p_1, p_2, \ldots p_N$, which are present after the edge of the partial blood vessel branches last, by using positional relationships between plural terminal end points $p_1, p_2, \ldots p_N$ and center line L of large intestine region C. The dominated region identification unit 37 obtains cross sections that pass through two outermost corresponding points of the determined plural corresponding points $l_1, l_2, \ldots l_M$, respectively, and that are orthogonal to center line L. Here, the term "outermost" refers to outermost corresponding points on center line L. The dominated region identification unit 37 identifies a part of large intestine region C between the cross sections, as dominated region FC (S7).

Further, the image generation unit 38 generates, from three-dimensional image D, display image I representing dominated region FC and the rest of large intestine region C in a visually distinguishable manner from each other (S8). Generated display image I is displayed on a display of the surgery assistance apparatus 3 (S9).

As described above, according to the surgery assistance apparatus 3 of the embodiment of the present disclosure, with respect to an arbitrary partial blood vessel in the whole blood vessel dominating a tubular organ, dominated region FC dominated by the partial blood vessel is identified. This region represents a range that is sufficiently large as a target region of excision when excision is performed by clipping the partial blood vessel or the like. Therefore, a doctor can appropriately and easily determine, based on this identified dominated region, a part to be removed in excision.

In the aforementioned embodiment, a corresponding point on center line L corresponding to a terminal end point of blood vessel V is obtained by obtaining a point on the surface of large intestine region C at a shortest distance from the terminal end point, and by obtaining a point on center line L at a shortest distance from the obtained point. However, it is not necessary that the corresponding point is determined in such a manner, and a point on center line L at a shortest distance from the target terminal end point may be determined, as the corresponding point corresponding to the terminal end point.

In the aforementioned embodiment, cross sections that pass through two outermost corresponding points of plural corresponding points determined on center line L, respectively, and that are orthogonal to center line L are obtained. Further, a part of large intestine region C between the cross sections is identified as dominated region FC. Instead of the two outermost corresponding points themselves, cross sections that pass through points in the vicinities of the two outermost corresponding points, respectively, and that are orthogonal to center line L may be obtained. Further, a part of large intestine region C between the cross sections may be identified as dominated region FC. As a point in the vicinity of the corresponding point, it is desirable to use a point in the range of 30 mm in the direction of the center line from the corresponding point. At this time, the positions of points in the vicinities of the corresponding points in the direction of the center line (corresponding to positions of cross sections orthogonal to center line L) may be determined in such a manner that the dominated region becomes larger as the partial blood vessel has a greater representative value of diameter. When the dominated region is determined by using points in the vicinities of the outermost corresponding points in this manner, it is desirable to use points that are located in the vicinities of the outermost corresponding points and toward the outside of the outermost corresponding points.

What is claimed is:

1. A surgery assistance apparatus comprising:
an organ region extraction unit that extracts a tubular organ region from a three-dimensional image obtained by imaging a tubular organ and a blood vessel dominating the tubular organ;
a blood vessel region extraction unit that extracts a blood vessel region dominating the tubular organ from the three-dimensional image;
a branching structure extraction unit that extracts a branching structure of the blood vessel from the extracted blood vessel region;
a dominated region identification unit that identifies, with respect to an arbitrary partial blood vessel corresponding to an upper edge branching at least once to reach an edge including a terminal end of the extracted branching structure, a dominated region in the tubular organ region that is dominated by the arbitrary partial blood vessel by using positional relationships between a plurality of terminal end points present after the edge of the arbitrary partial blood vessel branches last and the tubular organ region; and
a center line extraction unit that extracts a center line of the tubular organ region,
wherein the dominated region identification unit determines a corresponding point on the center line corresponding to each of the plurality of terminal end points by using positional relationships between the plurality of terminal end points and the center line, and obtains cross sections that pass through two outermost corresponding points of the determined plurality of corresponding points, respectively, or points in the vicinities of the outermost corresponding points, respectively, and that are orthogonal to the center line, and identifies a part of the tubular organ region between the cross sections, as the dominated region.

2. The surgery assistance apparatus, as defined in claim 1, the apparatus comprising:
an image generation unit that generates, from the three-dimensional image, an image representing the identified dominated region and a rest of the tubular organ region in a manner visually distinguishable from each other.

3. The surgery assistance apparatus, as defined in claim 1, wherein the dominated region identification unit receives specification of an arbitrary position by a user on an upper edge branching at least once to reach an edge at a terminal end of the branching structure, and identifies, with respect to a partial blood vessel corresponding to the edge at the specified position, the dominated region dominated by the partial blood vessel.

4. A surgery assistance apparatus comprising:
an organ region extraction unit that extracts a tubular organ region from a three-dimensional image obtained by imaging a tubular organ and a blood vessel dominating the tubular organ;
a blood vessel region extraction unit that extracts a blood vessel region dominating the tubular organ from the three-dimensional image;
a branching structure extraction unit that extracts a branching structure of the blood vessel from the extracted blood vessel region; and
a dominated region identification unit that identifies, with respect to an arbitrary partial blood vessel corresponding to an upper edge branching at least once to reach an edge including a terminal end of the extracted branching structure, a dominated region in the tubular organ region that is dominated by the arbitrary partial blood vessel by using positional relationships between a plurality of terminal end points present after the edge of the arbitrary partial blood vessel branches last and the tubular organ region, wherein the dominated region identification unit determines a point on the center line at a shortest distance from each of the plurality of terminal end points, as a corresponding point corresponding to each of the plurality of terminal end points.

5. A surgery assistance apparatus comprising:
an organ region extraction unit that extracts a tubular organ region from a three-dimensional image obtained by imaging a tubular organ and a blood vessel dominating the tubular organ;
a blood vessel region extraction unit that extracts a blood vessel region dominating the tubular organ from the three-dimensional image;
a branching structure extraction unit that extracts a branching structure of the blood vessel from the extracted blood vessel region; and
a dominated region identification unit that identifies, with respect to an arbitrary partial blood vessel corresponding to an upper edge branching at least once to reach an edge including a terminal end of the extracted branching structure, a dominated region in the tubular organ region that is dominated by the arbitrary partial blood vessel by using positional relationships between a plurality of terminal end points present after the edge of the arbitrary partial blood vessel branches last and the tubular organ region, wherein the dominated region identification unit obtains a point on a surface of the tubular organ region at a shortest distance from each of the plurality of terminal end points, and determines a point on the center line at a shortest distance from the obtained point, as a corresponding point corresponding to each of the plurality of terminal end points.

6. The surgery assistance apparatus, as defined in claim 1, wherein the dominated region identification unit determines positions of the cross sections orthogonal to the center line in the direction of the center line in such a manner that the dominated region becomes larger as the partial blood vessel has a greater representative value of diameter.

7. The surgery assistance apparatus, as defined in claim 1, wherein the dominated region identification unit receives specification of an arbitrary position by a user on an upper edge branching at least once to reach an edge at a terminal end of the branching structure, and identifies, with respect to a partial blood vessel corresponding to the edge at the specified position, the dominated region dominated by the partial blood vessel, the apparatus comprising:
an image generation unit that generates, from the three-dimensional image, an image representing a partial blood vessel region corresponding to a segment from the specified position to all of terminal ends present after the specified position branches last and a rest of the blood vessel region in a manner visually distinguishable from each other and also representing the identified dominated region and a rest of the tubular organ region in a manner visually distinguishable from each other.

8. A surgery assistance method causing one or a plurality of computers to execute:
an organ region extraction procedure that extracts a tubular organ region from a three-dimensional image obtained by imaging a tubular organ and a blood vessel dominating the tubular organ;
a blood vessel region extraction procedure that extracts a blood vessel region dominating the tubular organ from the three-dimensional image;
a branching structure extraction procedure that extracts a branching structure of the blood vessel from the extracted blood vessel region;
a dominated region identification procedure that identifies, with respect to an arbitrary partial blood vessel corresponding to an upper edge branching at least once to reach an edge including a terminal end of the extracted branching structure, a dominated region in the tubular organ region that is dominated by the arbitrary partial blood vessel by using positional relationships between a plurality of terminal end points present after the edge of the arbitrary partial blood vessel branches last and the tubular organ region; and
a center line extraction procedure that extracts a center line of the tubular organ region,
wherein the dominated region identification procedure determines a corresponding point on the center line corresponding to each of the plurality of terminal end points by using positional relationships between the plurality of terminal end points and the center line, and obtains cross sections that pass through two outermost corresponding points of the determined plurality of corresponding points, respectively, or points in the vicinities of the outermost corresponding points, respectively, and that are orthogonal to the center line, and identifies a part of the tubular organ region between the cross sections, as the dominated region.

9. A non-transitory computer-readable recording medium having stored therein a surgery assistance program causing one or a plurality of computers to function as:
an organ region extraction unit that extracts a tubular organ region from a three-dimensional image obtained by imaging a tubular organ and a blood vessel dominating the tubular organ;
a blood vessel region extraction unit that extracts a blood vessel region dominating the tubular organ from the three-dimensional image;
a branching structure extraction unit that extracts a branching structure of the blood vessel from the extracted blood vessel region;
a dominated region identification unit that identifies, with respect to an arbitrary partial blood vessel corresponding to an upper edge branching at least once to reach an edge including a terminal end of the extracted branching structure, a dominated region in the tubular organ region that is dominated by the arbitrary partial blood vessel by using positional relationships between a plurality of terminal end points present after the edge of the arbitrary partial blood vessel branches last and the tubular organ region; and
a center line extraction unit that extracts a center line of the tubular organ region,
wherein the dominated region identification unit determines a corresponding point on the center line corresponding to each of the plurality of terminal end points by using positional relationships between the plurality of terminal end points and the center line, and obtains cross sections that pass through two outermost corresponding points of the determined plurality of corresponding points, respectively, or points in the vicinities of the outermost corresponding points, respectively, and that are orthogonal to the center line, and identifies a part of the tubular organ region between the cross sections, as the dominated region.

10. A surgery assistance method, comprising:
extracting a tubular organ region from a three-dimensional image obtained by imaging a tubular organ and a blood vessel dominating the tubular organ;
extracting a blood vessel region dominating the tubular organ from the three-dimensional image;
extracting a branching structure of the blood vessel from the extracted blood vessel region; and
identifying, with respect to an arbitrary partial blood vessel corresponding to an upper edge branching at least once to reach an edge including a terminal end of the extracted branching structure, a dominated region in the tubular organ region that is dominated by the arbitrary partial blood vessel by using positional relationships between a plurality of terminal end points present after the edge of the arbitrary partial blood vessel branches last and the tubular organ region, wherein the identifying step determines a point on the center line at a shortest distance from each of the plurality of terminal end points, as a corresponding point corresponding to each of the plurality of terminal end points.

11. A surgery assistance method, comprising:

extracting a tubular organ region from a three-dimensional image obtained by imaging a tubular organ and a blood vessel dominating the tubular organ;

extracting a blood vessel region dominating the tubular organ from the three-dimensional image;

extracting a branching structure of the blood vessel from the extracted blood vessel region; and identifying, with respect to an arbitrary partial blood vessel corresponding to an upper edge branching at least once to reach an edge including a terminal end of the extracted branching structure, a dominated region in the tubular organ region that is dominated by the arbitrary partial blood vessel by using positional relationships between a plurality of terminal end points present after the edge of the arbitrary partial blood vessel branches last and the tubular organ region, wherein the identifying step obtains a point on a surface of the tubular organ region at a shortest distance from each of the plurality of terminal end points, and determines a point on the center line at a shortest distance from the obtained point, as a corresponding point corresponding to each of the plurality of terminal end points.

12. A non-transitory computer-readable recording medium having stored therein a surgery assistance program causing one or a plurality of computers to execute:

extracting a tubular organ region from a three-dimensional image obtained by imaging a tubular organ and a blood vessel dominating the tubular organ;

extracting a blood vessel region dominating the tubular organ from the three-dimensional image;

extracting a branching structure of the blood vessel from the extracted blood vessel region; and identifying, with respect to an arbitrary partial blood vessel corresponding to an upper edge branching at least once to reach an edge including a terminal end of the extracted branching structure, a dominated region in the tubular organ region that is dominated by the arbitrary partial blood vessel by using positional relationships between a plurality of terminal end points present after the edge of the arbitrary partial blood vessel branches last and the tubular organ region, wherein the identifying step determines a point on the center line at a shortest distance from each of the plurality of terminal end points, as a corresponding point corresponding to each of the plurality of terminal end points.

13. A non-transitory computer-readable recording medium having stored therein a surgery assistance program causing one or a plurality of computers to:

extracting a tubular organ region from a three-dimensional image obtained by imaging a tubular organ and a blood vessel dominating the tubular organ;

extracting a blood vessel region dominating the tubular organ from the three-dimensional image;

extracting a branching structure of the blood vessel from the extracted blood vessel region; and identifying, with respect to an arbitrary partial blood vessel corresponding to an upper edge branching at least once to reach an edge including a terminal end of the extracted branching structure, a dominated region in the tubular organ region that is dominated by the arbitrary partial blood vessel by using positional relationships between a plurality of terminal end points present after the edge of the arbitrary partial blood vessel branches last and the tubular organ region, wherein the identifying step obtains a point on a surface of the tubular organ region at a shortest distance from each of the plurality of terminal end points, and determines a point on the center line at a shortest distance from the obtained point, as a corresponding point corresponding to each of the plurality of terminal end points.

* * * * *